United States Patent [19]

Kaswan

[11] Patent Number: 4,649,047
[45] Date of Patent: Mar. 10, 1987

[54] OPHTHALMIC TREATMENT BY TOPICAL ADMINISTRATION OF CYCLOSPORIN

[75] Inventor: Renee Kaswan, Athens, Ga.

[73] Assignee: University of Georgia Research Foundation, Inc., Athens, Ga.

[21] Appl. No.: 713,701

[22] Filed: Mar. 19, 1985

[51] Int. Cl.[4] ..................... A61K 37/00; A61K 31/74
[52] U.S. Cl. ........................................ 424/78; 514/11; 514/885; 514/912
[58] Field of Search .................... 424/78; 514/885, 11, 514/912, 914

[56] References Cited
PUBLICATIONS

Chem. Abst. 102:214587v (1985)—Mosteller et al.
Chem. Abst. 102:125267y (1985)—Williams et al.
Chem. Abst. 102:89788h (1985)—Boisjolv et al.
Chem. Abst. 101:103683h (1984)—Chan et al.
Chem. Abst. 101:16979v (1984)—Mannis et al.
Chem. Abst. 97 84951z (1982)—Nussenblatt et al.
Chem. Abst. 97 439c (1982)—Kana et al.
Chem. Abst. 94 185,629u (1981)—Nussenblatt et al.
Amer. J. Ophthal. 96(3) 275–282 (1983)—Nussenblatt et al.
Biosjoly et al., Prophylactic Topical Cyclosporine in Experimental Herpetic Stromal Keratitis, Arch Ophthalmol, 102, 1804, Dec. 1984.
Mosteller et al., Penetration of Topical Cyclosporine into the Rabbit Cornea, Aqueous Humor, and Serum, Arch. Ophthalmol, 103, 101, Jan. 1985.
Nussenblatt et al., Cyclosporin A Therapy in the Treatment of Intraocular Inflammatory Disease Resistant to Systemic Corticosteroids and Cytotoxic Agents, American Journal of Ophthalmology, 96, 275, Sep. 1983.
Kaswan et al., Intraocular Penetration of Cyclosporin in Rabbits, ARVO Abstracts, Investigation Ophthalmol. Supp. 25, 3, p. 38, 1984.

Primary Examiner—Douglas W. Robinson
Attorney, Agent, or Firm—Oblon, Fisher, Spivak, McClelland, & Maier

[57] ABSTRACT

The present invention relates to a method for the treatment of either phacoanaphylactic endophthalmitis or uveitis by administering at least one cyclosporin topically to the eyes. Topical application of cyclosporin provides cyclosporin to the anterior chamber, the posterior chamber and the vitreous body of the eye.

20 Claims, 6 Drawing Figures

OPHTHALMIC TREATMENT BY TOPICAL ADMINISTRATION OF CYCLOSPORIN

BACKGROUND OF THE INVENTION

1. Field of the Invention

The present invention relates to cyclosporin treatment of traumatic or surgical phacoanaphylaxis endophthalmitis, or uveitis.

2. Description of the Prior Art

Phacoanaphylactic endophthalmitis and uveitis are diseases of the eye which can be located throughout the eye; in both the posterior and anterior chambers of the eye as well as the vitreous body.

Uveitis, the inflammation of the uvea, is responsible for about 10% of the visual impairment in the United States. Phacoanaphylactic endophthalmitis is a human autoimmune disease.

Panuveitis refers to inflammation of the entire uveal (vascular) layer of the eve. Posterior uveitis generally refers to chorioretinitis and anterior uveitis refers to iridocyclitis. The inflammatory products (i.e., cells, fibrin, excess proteins) of these inflammations are commonly found in the fluid spaces of the eye, i.e., anterior chamber, posterior chamber and vitreous space as well as infiltrating the tissue imminently involved in the inflammatory response. Uveitis may occur following surgical or traumatic injury to the eye; as a component of an autoimmune disorder, i.e., rheumatoid arthritis, Behcet's disease, ankylosing spondylitis, sarcoidosis; as an isolated immune mediated ocular disorder, i.e., pars planitis, iridocyclitis etc., unassociated with known etiologies; and following certain systemic diseases which cause antibody-antigen complexes to be deposited in the uveal tissues. Together these disorders represent the non-infectious uveitities.

The normal eye is protected from immune surveillance by blood barriers which do not allow free migration of cells or proteins into the eye. When the eye is injured or when vasculitis occurs, the internal ocular structures are exposed to the general immune system and frequently elicit autoimmune responses.

Phacoanaphylaxis is a severe form of uveitis in which the lens is the causitive antigen. The lens proteins are normally secluded by the lens capsule since before birth. When these proteins are released into the eye by injury or surgery or occasionally during cataract development, they can become intensely antigenic and incite an autoimmune response. If the response is moderate it is seen as a chronic uveitis. If it is very fast in progression they eye becomes severely inflamed in all segments. This latter response is named phacoanaphylaxis.

Cyclosporins are unique immunosuppressive agents derived from an extract of soil fungi. Cyclosporine A was first proposed for use as an antifungal agent but its immunosuppressive effects were found to be more marked than its antibiotic potential. This drug inhibits the generation of effector T-lymphocytes without inhibiting the expression of suppressor lymphocytes.

Cyclosporin's immunosuppressive properties has led to its use in immune system related diseases. In ophthalmic applications, cyclosporin has been used topically for the treatment of eye surface (e.g., cornea) related diseases.

For example, Hunter et al (*Clin. Exp. Immunol.* (1981), 45, pp. 173-177) has administered cyclosporin topically in a rabbit model of corneal graft rejection with positive results. These effects were found to be attributable to T-cell suppression within the eye or within systemic compartments such as blood or lymph.

Boisjoly et al (Arch. Ophthalmol. (1984) 102:1804-1807) have reported that topical application of Cyclosporine had a beneficial prophylactic effect towards the treatment of severe herpetic stromal keratitis.

Mosteller et al (*Investigative Ophthalmol.* (1984) Supp. 23, 3, p. 38) propose the potential suppression of deleterious ocular immune reactions such as the eye surface cornea allograft reaction by applying a single dose of a 10% Cyclosporine A ointment in the lower culde-sac of rabbit eyelids.

In other ophthalmic applications, where the disease being treated is not limited to the eye surface, cyclosporin has been used systemically.

For example, Nussenblatt et al (*Amer. J. Ophthamol.* (1983), 96, pp. 275-282) has reported clinical improvement in some patients with noninfectious posterior uveitis following systemic treatment with Cyclosporin.

To date, uveitis has been treated by systemic administration of cyclosporin since this disease is not limited to the eye surface. However, systemic therapy with cyclosporin has serious drawbacks. First there is a high risk of adverse responses when cyclosporin is used systemically. For example, cyclosporin increases the severity of epithelial disease when antiviral coverage is not provided. Cyclosporine used systemically has also been associated with a high incidence of renal toxicity, some cases of hepatotoxicity, increased incidence of lymphoid tumors and increased incidence of opportunistic infections. It is only slightly less toxic than other immunosuppressive agents i.e., cyctoxan, aziothioprine which in addition to causing increased incidence of infections, are more irreversible in their effects than is cyclosporine. The systemic side effects of cyclosporine are so severe and so common that they preclude its use to life-threatening or in some cases severe sight-threatening disease. Finally, systemic application of cyclosporin is limited by its prohibitive cost.

Prior art understanding of the activity of cyclosporin towards ophthalmic traumatic uveitis has however rested on the theory that total body immunosuppression was necessary for efficacy. By requiring systemic administration in cyclosporin treatment of opthalmic diseases not limited to the eye surface, a patient has heretofore been required to assume a high risk of adverse immunological responses, this risk naturally being accompanied by high treatment expense due to the quantities of cyclosporin required in systemic therapy.

Accordingly there exists a strong need for the elimination of the undesirable physiological and economic problems associated with cyclosporin treatment of phacoanaphylactic endophthalmitis and uveitis, while maintaining the advantageous therapeutic properties of this treatment.

Applicants have now surprisingly discovered that although current ocular pharmacology dictates that topical medications in general are not useful for the treatment of opthalmic diseases found in the posterior or vitreous segments of the eye (see, e.g., Maurice et al, *Ocular Pharmacokinetics, in Pharmacology of Eye*, Sears, M. L., editor, Springer-Verlag publisher, New York (1984), pp. 19-102), the topical administration of a cyclosporin to the eye is efficatious in the treatment of phacoanaphylactic endophthalmitis or uveitis found either in the anterior or posterior chambers of the eye or in the vitreous body of the eye.

SUMMARY OF THE INVENTION

Accordingly it is an object of this invention to provide a method for the treatment of phacoanaphylactic endophthalmitis.

It is another object of this invention to provide a method for the treatment of uveitis.

It is another object of this invention to provide a cyclosporin-based treatment of phacoanaphylactic endophthalmitis without the accompanying adverse physiological responses and economic difficulties.

It is another object of this invention to provide a cyclosporin-based treatment of uveitis without the accompanying adverse physiological responses and economic difficulties.

It is another object of this invention to provide a method for the treatment of phacoanaphylactic endophthalmitis in the anterior chamber of the eye.

It is another object of this invention to provide a method for the treatment of uveitis in the anterior chamber of the eye.

It is another object of this invention to provide a method for the treatment of phacoanaphylactic endophthalmitis in the posterior chamber of the eye.

It is another object of this invention to provide a method for the treatment of uveitis in the posterior chamber of the eye.

It is another object of this invention to provide a method for the treatment of opthalmic diseases, such as phacoanaphylactic endophthalmitis or uveitis, found in the vitreous body of the eye.

Applicants have discovered that these objects of the present invention are surprisingly satisfied by the topical application of at least one cyclosporin to the eye. Applicants have discovered that the topical application of at least one cyclosporin in a suitable medical excipient is advantageously useful for the treatment of phacoanaphylactic endophthalmitis or uveitis throughout the globe of the eye.

BRIEF DECRIPTION OF THE FIGURES

A more complete appreciation of the invention and many of the attendant advantages thereof will be readily obtained as the same becomes better understood by reference to the following detailed description when considered in connection with the accompanying figures, wherein.

DESCRIPTION OF THE PREFERRED EMBODIMENTS

Figure 1A:
FIG. 1a is a photograph of the clinical appearance of endophthalmitis in a pre-sensitized and untreated rat eye 9 days after lens injury.

The present invention provides a method for the treatment of phacoanaphylactic endophthalmitis or uveitis occuring throughout the globe of the eye by topical administeration of a cyclosporin to the eye. This topical application of a cyclosporin provides cyclosporin treatment for the anterior chamber, the posterior chamber and the vitreous body of the eye.

Phacoanaphylactic endophthalmitis and uveitis are diseases of the eye which can be found throughout the eye. In accordance with prior art wisdom, uveitis has been treated via systemic administration of cyclosporin. No treatment method for phaconaphylactic endophthalmitis has been reported. Systemic therapy of any disease with cyclosporin suffers from at least two major drawbacks; a high risk of immunologically related adverse responses and high cost.

Against the wisdom of the prior art, the present inventors have surprisingly discovered that systemic administration of cyclosporin is not necessary for the treatment of uveitis, and additionally that phacoanaphylactic endophthalmitis can be treated. This present invention relates to the unexpected discovery that topical cyclosporin administration to the eyes is very efficatious in the treatment of both of these diseases in various regions of the eye.

The present inventors investigated the levels of cyclosporin present in various parts of the eye as a function of varying administration methods. In this investigation the ocular penetration of cyclosporine following topical or oral administration was determined using radio-immune assays (RIA).

The results of this study, tabulated in the Table below, are given to illustrate the invention only and are not intended to impose any limit thereon.

TABLE

| | Route of Cyclosporine administration vs Tissue Level Cyclosporine (ng/gm) | | | | | | |
|---|---|---|---|---|---|---|---|
| | Tissue Cornea | Aqueous | Lens | Anterior Vitreous | Posterior Vitreous | Blood | # Eyes |
| Oral 20 mg/kg/day × 4 days | <250 | <60 | <250 | <60 | <60 | 617 | 12 |
| Ophthalmic 2% oil Q 15 min × 6 | 6,640 (3,600–11,600) | <60 (ND) | <250 | <60 | <60 | ND | 8 |
| Ophthalmic 2% ointment Q 15 min × 6 | 9,750 (5,600–14,400) | <60 (20) | <250 | 325 (80–1,450) | 690 (425–800) | ND | 6 |
| Ophthalmic 2% oil | 15,140 (7,300–27,500) | <60 (24) | <250 | 2,400 (500–4,700) | 400 (250–525) | ND | 8 |

TABLE-continued

| | Route of Cyclosporine administration vs Tissue Level Cyclosporine (ng/gm) | | | | | | |
|---|---|---|---|---|---|---|---|
| | Tissue Cornea | Aqueous | Lens | Anterior Vitreous | Posterior Vitreous | Blood | # Eyes |
| QID × 21 d Ophthalmic 2% oil QID × 21 d | 7,400 (7,000–8,200) | 200 (180–200) | 1,340 | 875 (800–950) | 720 (640–800) | ND | 2 |
| | | | | | | | Total = 36 eyes |

Legend:
ND = not determined
QID = 4 times daily
Q 15 min × 6 = every 15 minutes for 6 applications
d = day
ng/gm = nanograms per gram or ml of ocular tissue
values in parenthesis represent the range of the measurements As can be seen from the Table the topical administration of Cyclosporine at varying dosage schedules provides much greater levels of cyclosporine in various tissues of the eye than is available through oral administration.

Thus topical administration has surprisingly been found to be an excellent method for providing cyclosporin in much greater concentrations to the cornea, lens, anterior vitreous, posterior vitreous, iris and ciliary body regions of the eye, where these higher concentrations of cyclosporin provide a much more effective treatment for phacoanaphylactic endophthalmitis and uveitis in these regions of the eye. Additionally since by its very nature, topical administration does not require cyclosporine dispersion throughout the system as is the case with systemic administrations, the present invention provides a means for directing cyclosporin to the desired location.

Figure 3A:
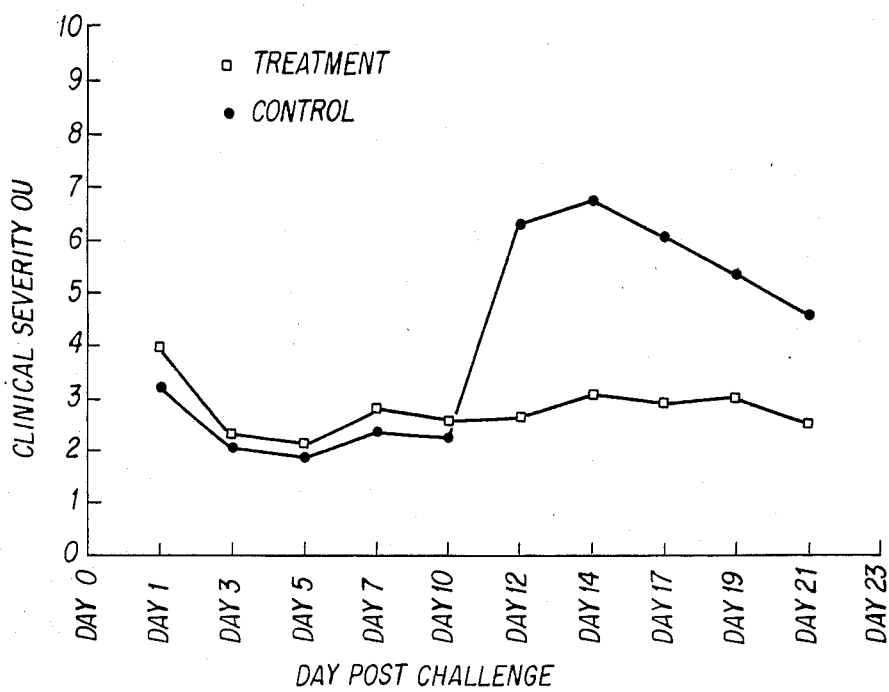
FIG. 3a is a graphic representation of the average intraocular inflammation observed in rabbit eyes treated with a topical application of 2% cyclosporine (○) compared to untreated eyes (●).
Figure 3B:
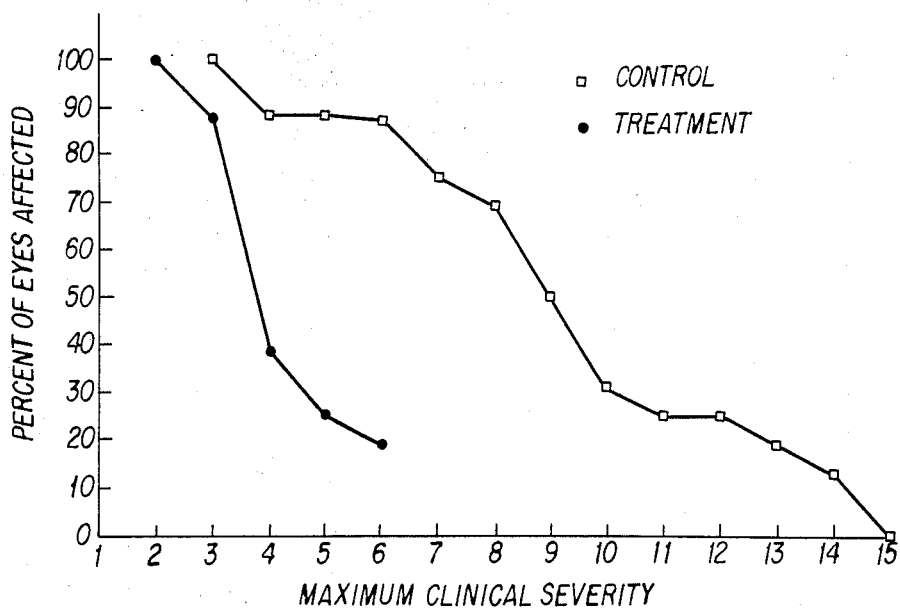
FIG. 3b illustrates the data of FIG. 3a in another form; the percentage of eyes reaching a peak of inflammation at any point during a period of 15 days.

The graphs of FIGS. 3a and 3b demonstrate the efficacy of topical cyclosporine administration.

The graph of FIG. 3a plots the intraocular inflammation produced by the intravitreal injection of human serum albumin into rabbit eyes. In this study 16 rabbits, 32 eyes, were used. Eight rabbits received no treatment bilaterally, the other eight rabbits received treatment via the topical administration of 2% cyclosporine in oil bilaterally. The degree of intraocular inflammation was graded clinically 3 times per week for 3 weeks. The scale used to evaluate the eyes is reproduced on page 22. The degree of inflammation, 0 to 4, of each segment of the eye was summed on each day, giving a possible range of inflammation of 0–20 per day. The data graphed represents the average daily inflammation seen in the untreated eyes (●) versus the treated eyes (○).

Both untreated and treated eyes developed a low level of inflammation. The inflammation in the treated eyes never exceed this low level base. By contrast, the untreated eyes which began with the same low level of inflammation had become severely inflamed by the tenth day. This severe inflammation began at about 7 days, peaked at 14 days, and then subsided naturally after day 21.

The graph of FIG. 3b illustrates the same data differently. FIG. 3b indicates the percentage of eyes reaching a peak inflammation at any point during the experiment. As illustrated, the peak inflammation seen in any untreated eye was 6.0 and the lowest peak level was 2.0. 75% of the treated rabbit eyes never developed any inflammatory response above 5/20. By contrast, the worst inflammatory response in the untreated eyes reached a peak inflammation of 15/20 or greater at some point. The higher degree of inflammation observed in each untreated eye results in a concomitantly greater risk of permanent visual damage.

In accordance with the present invention, the cyclosporin may be used in any efficatious concentration, e.g., 0.1 to saturation (e.g., >20 wt %) in a medically suitable excipient. Such medically suitable excipients may be, for example, animal oil, vegetable oil, an appropriate organic or aqueous solvent, a natural or synthetic polymer or an appropriate membrane.

Examples of these medically suitable excipients may be, for example, olive oil, arachis oil, castor oil, mineral oil, petroleum jelly, dimethyl sulphoxide, an alcohol (e.g., ethanol, n-propyl alcohol, iso-propyl alcohol), methylcellulose, liposomes or liposome-like products or a silicone fluid. Dimethyl sulphoxide and olive oil are especially preferred. Of course mixtures of at least two of any of the excipient may be used.

An example of a useful polymeric excipient may be, e.g., polyoxyethylated castor oil.

Examples of medically suitable membranes which may be used in the practice of this invention are: microdone, an artificial lipid membrane, polyvinylalcohol or methyl cellulose.

The cyclosporin may be topically administered as an ophthalmic drop or ophthalmic ointment containing an effective amount of the cyclosporin. Concentrations of 0.10 to 20 wt % of cyclosporin may be used.

In accordance with the method of the present invention, cyclosporin may be topically administered in any quantity required to provide the degree of treatment needed. Cyclosporin within the range of 5 microliters to 1000 microliters may be used, e.g., 5 microliters to 1 milliliter of solution or ointment.

The cyclosporin which are useful in the practice of the present invention may be both natural or synthetic cyclosporin. For example, cyclosporin A may be used in the practice of the present invention. Other forms of cyclosporins (e.g., isomers) may also be used. Mixtures of at least two different cyclosporin may be used. The only thing that is required, is that the cyclosporin possess the required activity vis-a-vis phacoanaphylactic endophthalmitis or uveitis.

The method of the present invention is useful in that it can locally prevent activation of a presystemic response. It is useful therapy for traumatic phacoanaphylaxis and iatrogenic lens induced uveitis such as occurs in extracapsular cataract surgery.

Other features of the invention will become apparent in the course of the following descriptions of exemplary embodiments which are given for purposes of illustration of the invention and are not intended to be limiting thereof.

In the following examples tests were performed on animals which are well known models for human opthalmic problems, and/or diseases.

Referring now to the figures, where like reference numerals or letters designate identical or corresponding parts throughout the several views, FIG. 1a presents the clinical appearance of endophthalmitis in a pre-sensitized untreated rat eye 9 days after lens injury. From this photograph it can be seen that neovascularization of the cornea and dense leukophilic reaction in the corneal stroma obscure the inner eye.

Figure 1B:
FIG. 1b is a photograph of the microscopic appearance ($\times 23$) of phacoanaphylaxis from an untreated control rat eye.

FIG. 1b presents the microscopic appearance of phacoanaphylaxis from an untreated control rat eye. Zonal distribution of neutrophils and macrophages are apparent around the ruptured anterior lens capsule (see arrow in the figure). Dense lymphocytic effusion fills the vitreous and aqueous space as well as infiltrating the uveal tissue anteriorly and posteriorly. A fibrocytic cyclitic membrane (C) has formed posterior to the lens (1). The globe of the eye is approximately 30% reduced in size due to phthisis.

Figure 2A:
FIG. 2a is a photograph of the clinical appearance, at 14 days, of a rat eye given topical cyclosporine therapy beginning on the day of lens injury.

FIG. 2a is the clinical appearance at 14 days of a rat eye given topical cyclosporin therapy beginning on the day of lens injury. Apparent iris blood vessels are normally visualized due to albinism. The eye is otherwise unaffected clinically.

Figure 2B:
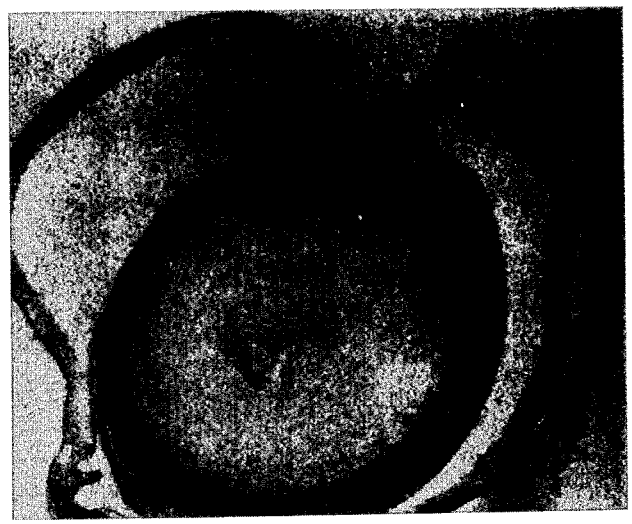
FIG. 2b is a photograph of a microscopic section ($\times 23$) of a rat eye 14 days following Cyclosporine topical therapy.

FIG. 2b is a microscopic section of a rat eye following 14 days of cyclosporine topical therapy. The anterior lens capsule is ruptured. Subjacent cortical vacuolization and early cataractous change is evident (see arrow in figure). A minimal number of lymphocytes are seen in the iris.

EXAMPLE 1

The lens-induced granulomatous endophthalmitis (ELGE) model (See Marak, G.E. et al, *Ophthal. Res.* (1978) 10:30) was reproduced in 4/8 control eyes. In contrast, eyes treated topically with Cyclosporine uniformly failed to develop marked cellular infiltration following rupture of the lens capsule. Rats treated with systemic Cyclosporine showed modest protection compared to untreated rats. Although no animals were followed after Cyclosporine withdrawal, it is likely that lens removal could alleviate a need for chronic treatment. Based on the prophylactic effect of topical cyclosporin against development of ELGE, topical Cyclosporine penetration the globe in therapeutic levels is indicated.

Eleven female adult Wistar Furth rats were immunized subcutaneously on 3 occasions every two weeks with 1 ml of a 50:50 mixture of 10 mg homologous lens protein in saline and Freund's complete adjuvant. Two weeks after the last immunization, the rats were anestitized with Ketamine HCl 10 mg/kg intramuscularly. With the aid of a disecting microscope, a sterile 26g needle was introduced through the central cornea and a "Z" shaped anterior lens capsule tear was formed by manipulating the needle in each right eye. Tobrex ® ointment was applied post operatively and tetracycline 400 mg/liter was added to the drinking water.

Four rats served as controls and received no antiinflammatory drugs. Four rats received 10 mg/kg cyclosporin 2% in olive oil by gavage beginning two hours post-operatively. Three rats received 15 μl of 2% Cyclosporine in olive oil applied topically 9-12 times daily for three days following injury, then 4 times daily thereafter. After 7 days, the left lens capsules were torn as above in all rats. In the second surgical trial, rats in treatment groups began Cyclosporine per os or topically three hours prior to injury of the second eye.

All rats were examined periodically with a slit lamp or disecting microscope. Fourteen days after the initial surgery all rats were euthanized with halothane ® anesthetic. Both eyes were fixed in formalin, processed by standard methods, and stained with hematoxylin and eosin.

Immediately post-operatively, all rats developed a plasmoid aqueous and miosis lasting 48 to 72 hours. Six of eight untreated eyes continued to develop severe uveitis beginning with hypopyon and corneal edema. Four of eight developed secondary glaucoma with buphthalmos. Progression continued with development of corneal abcessation, neovascularization and panophthalmitis (FIG. 1a). Four eyes progressed to a phthesis bulbi. Histopathology of these eyes revealed a aseptic gramulomatous panophthalmitis. A zonal distribution of neutrophils and macrophages occurred around the ruptured lens capsule where early cataractrous changes were evident. A cyclictic membrane formed behind the lenses. The anterior chamber, iris, vitrus humor and retina were densely infiltrated with lymphocytes (FIG. 1b). On histopathologic examrnation, two untreated eyes have moderate acute anterior uveitis. Two untreated eyes had no inflammation at seven or fourteen days post injury.

None of the 6 eyes treated with topical Cyclosporine developed prolonged or destructive inflammation (FIG. 2a). At forty-eight hours post operatively, one eye had a small central corneal abcess which resolved by day five. On histopalogic examination, the lens capsules were torn and the subjacent lens cataractous, but little or no inflammation was associated with the injury (FIG. 2b). No difference was noted between the eye begun on therapy 2 hours pre or post trauma.

The rats given oral Cyclosporine developed uveitis intermediate in intensity between controlled and topically treated eyes. Clinically the degree of anterior uveitis appeared most marked at 4 to 6 days in this group after which sometimes lessened. After 7 to 14 days, histopathologic sections of orally treated eyes revealed ⅜ with phacoanaphylaxis, ⅜ with anterior uveitis and 2/8 not inflammed.

EXAMPLE 2

Cyclosporin distribution as a function of administration method

Intraocular concentrations of cyclosporine as a function of administration route was determined for the blood and the following various eye compartments: cornea, aqueous, lens, anterior vitreous and posterior vitreous.

Methods:

Oral 20 mg/kg/day for 4 or ten days. No intraocular cyclosporine was detected.

Topical application of 17 microliters of 2% cyclosporine in olive oil, applied every 15 minutes for 6 applications, followed by a period of 60 minutes to allow absorption.

Topical application of 2% cyclosporine in oil every 60 minutes for 6 applications, followed by 60 minutes to allow absorption.

Topical application of 100 microliters of 2% cyclosporine in petroleum jelly and mineral oil, applied every 15 minutes for 6 applications, followed by a period of 60 minutes to allow absorption.

Topical application of 2% cyclosporin in olive oil 4 times daily for 10 days.

Following dosage the rabbits were euthanized and the eyes were enucleated and frozen. The eyes were dissected into their component parts. These were then digested in collagenase and the solutions were analyzed with Radioimmunoassay for cyclosporine content.

Results:

The Table below tabulates the number of eyes subjected to each dosage regime and the range of values obtained for each compartment.

TABLE

| | Route of Cyclosporine Administration vs Tissue Level Cyclosporine (ng/gm) | | | | | | |
|---|---|---|---|---|---|---|---|
| | Tissue Cornea | Aqueous | Lens | Anterior Vitreous | Posterior Vitreous | Blood | # Eyes |
| Oral 20 mg/kg/day × 4 days | <250 | <60 | <250 | <60 | <60 | 617 | 12 |
| Ophthalmic 2% oil Q 15 min × 6 | 6,640 (3,600–11,600) | <60 (ND) | <250 | <60 | <60 | ND | 8 |
| Ophthalmic 2% oil Q 60 min × 6 | 9,750 (5,600–14,400) | <60 (ND) | <250 | 325 (80–1,450) | 690 (425–800) | ND | 6 |
| Ophthalmic 2% oil Q 15 min × 6 | 15,140 (7,300–27,500) | <60 (24) | <250 | 2,400 (500–4,700) | 400 (250–525) | ND | 8 |
| Ophthalmic* 2% oil QID × 10 d | 7,400 (7,000–8,200) | 200 (180–200) | 178 | 875 (800–950) | 720 (640–800) | ND | 10 |
| | | | | | | | Total = 36 eyes |

*iris and ciliary body 749, retina 483.
Legend:
ND = not determined
QID = 4 times daily
Q 15 min × 6 = every 15 minutes for 6 applications
d = day
ng/gm = nanograms per gram or ml of ocular tissue
values in parenthesis represent the range of the measurements

EXAMPLE 3

In another experiment, 1% tritiated cyclosporine in oil was applied to the eyes every 15 minutes for 6 applications followed by 60 minutes to allow for absorption. 3 rabbits, 6 eyes, were used. The eyes were frozen, dissected and digested as above, but this time the RIA was not necessary since the radiolabel was incorporated into the dose applied. The samples were counted in liquid scintillation and the absorbed cyclosporine calculated from the relative radioactivity of each sample. In this experiment the corneal level was 5792 ng/gm, aqueous 143, Iris 95, vitreous 190, lens 0, retina 0. These levels are essentially those found in the 1st dosage regimen which used a similar interval but a two-fold higher concentration. This final experiment confirms the accuracy of the method of example 2.

EXAMPLE 4

Effectiveness of topical cyclosporine administration

Sixteen rabbits, 32 eyes were injected intravitreally on day 1 with 500 micorgrams of human serum albumin. Eight rabbits received no treatment. The other rabbits received 10 microliter of 2% cyclosporine in olive oil applied topically to both eyes 4 times daily beginning 1 hour after albumin injection. The degree of intracular inflammation produced was graded clinically 3 times a week for 3 weeks. The scale used to evaluate the eyes is given below.

| Scheme for Grading Uveitis in Animals injected with Human Serum Albumin | | | | | |
|---|---|---|---|---|---|
| Clinical observation | 0 | +1 | +2 | +3 | +4 |
| Ciliary-scleral injection | none | trace | mild | moderate | severe |
| Corneal clarity | clear | trace edema | mild edema | moderate | severe |
| Iris injection | none, pupil normal | trace | mild | moderate | severe, pupil fixed |
| Anterior chamber haze | clear | trace | mild | moderate ± few KP's | Opaque ± many KP's |
| Viteous & retina | Chorioretinal detail sharp | Chorioretinal detail visible but blurred | fair red reflex | poor red reflex | no red reflex |

Note:
Corneal neovascularization
retinal detachments
hypopyon
hyphena
fibrin deposition
iris bombe, depth of anterior chamber The degree of inflammation, 1–4 of each regiment of the eye was summed on each day, giving a possible range of inflammation of 0–20 per day. The data obtained is provided in FIGS. 3a and 3b.

Method (for Example 4):

Human serum albumin (HSA) induced uveitis was initiated bilaterally (OU) in 16 adult female albino rabbits. The animals received ketamine 25 mg/kg and xylazine 3 mg/kg IM 20 minutes prior to intraocular injections. To prevent vitreal extravasation an aqueous paracentesis was performed with a 30-gauge needle and 0.10 ml aqueous was removed prior to intravitreal injection of 500 micrograms of HSA in 0.10 ml of saline. The subsequent induction and resolution of uveitis were observed by slit-lamp examination and indirect ophthalmoscopy 3 times per week. The degree of inflammation in eyes was graded and summed to give a total daily score of 0–20/eye. All observations were performed without knowledge of treatment group.

The treatment group consisted of 8 rabbits which received 10 microliters of cyclosporine (Sandimmune ®), 2% in olive oil applied to the dorsal limbus OU, 4 times daily (QID) beginning 1 hour post HSA injection. The remaining 8 rabbits received no therapy (positive control group). As a negative control group, an additional 4 rabbits were injected intravitreally OU with 0.10 ml of saline without HSA and treated unilaterally with 2% Cs-A as above. Oxytetracycline 1 gm/gallon was added to the drinking water of all rabbits as prophylaxis for Pasteurella respiratory infections. All animal utilization adhered to the ARVO resolution on the use of animals in research. The limulus lysate test (Whittaker Bioproducts Inc) was performed on 3 commercial preparations of HSA and found to be positive in all samples. The HSA used for all rabbits for induction of uveitis had 0.17 endotoxin units /mg HSA.

Obviously, numerous modifications and variations in the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for the treatment of phacoanaphylactic endophthalmitis in the anterior or posterior segment of an eye which comprises administering a therapeutically effective amount of a cyclosporin topically to said eye.

2. A method for the treatment of uveitis in the anterior or posterior segment of an eye which comprises administering a therapeutically effective amount of a cyclosporin topically to said eye.

3. The method of claim 1 wherein from 0.1 to 50 wt % of cyclosporin in a medically suitable excipient is used.

4. The method of claim 2 wherein from 0.1 to 50 wt. % of cyclosporin in a medically acceptable excipient is used.

5. The method of claim 3 wherein the medically suitable excipient comprises animal or vegetable oil.

6. The method of claim 4 wherein the medically suitable excipient comprises animal or vegetable oil.

7. The method of claim 3 wherein the medically suitable excipient comprises olive oil, arachis oil, castor oil, mineral oil, petroleum jelly, dimethyl sulphoxide, an alcohol, silicone fluid or a mixture thereof.

8. The method of claim 4 wherein the medically suitable excipient comprises olive oil, arachis oil, liposome, castor oil, mineral oil, petroleum jelly, dimethyl sulphoxide, an alcohol, silicone fluid or a mixture thereof.

9. The method of claim 1 wherein the cyclosporin is a natural cyclosporin or a synthetic cyclosporin.

10. The method of claim 2 wherein the cyclosporin is a natural cyclosporin or a synthetic cyclosporin.

11. The method of claim 3 wherein the medically suitable excipient comprises polyvinyl alcohol, polyoxethylated castor oil or methyl cellulose or a mixture thereof.

12. The method of claim 4 wherein the medically suitable excipient comprises polyvinyl alcohol, polyoxethylated castor oil, methyl cellulose or a mixture thereof.

13. The method of claim 7 wherein the medically suitable excipient is dimethyl sulphoxide.

14. The method of claim 8 wherein the medically suitable excipient is dimethyl sulphoxide.

15. The method of claim 1, wherein Cyclosporin A is used.

16. The method of claim 2, wherein said cyclosporin is Cyclosporin A.

17. The method of claim 1, wherein said phacoanaphylactic endophthalmitis is traumatic phacoanaphylactic endothalmitis.

18. The method of claim 2, wherein said uveitis is iatrogenic-lens-induced uveitis.

19. A method for the treatment of a disorder caused by excessive immune activity in the anterior or posterior segment of an eye, which comprises topically administering to said eye an amount of a cyclosporin sufficient to reduce said immune activity.

20. A method for the treatment of a disorder caused by excessive immune activity in the vitrous body of an eye, which comprises topically administering to said eye an amount of a cyclosporin sufficient to reduce said immune activity.

* * * * *

UNITED STATES PATENT AND TRADEMARK OFFICE
CERTIFICATE OF CORRECTION

PATENT NO.   : 4,649,047
DATED        : March 10, 1987
INVENTOR(S)  : Renee Kaswan It is certified that error appears in the above-identified patent and that said Letters Patent is hereby corrected as shown below:

<u>Column 1,</u>
Line 3, insert:
-- This invention was made in part with U.S. government support under grant number R03EY05720-01 from the National Institutes of Health. The U.S. government has certain rights in this invention. --

Signed and Sealed this

Eighth Day of January, 2002

*Attest:*

JAMES E. ROGAN
*Attesting Officer*     *Director of the United States Patent and Trademark Office*